US009244056B2

(12) United States Patent
Kim et al.

(10) Patent No.: US 9,244,056 B2
(45) Date of Patent: Jan. 26, 2016

(54) INTEGRATED SAMPLING AND DISPENSING DEVICE

(75) Inventors: Byeong Chul Kim, Chuncheon-si (KR); Taek Kyu Oh, Cheongju-si (KR)

(73) Assignee: BODITECH MED INC., Gangwon-do (KR)

( * ) Notice: Subject to any disclaimer, the term of this patent is extended or adjusted under 35 U.S.C. 154(b) by 109 days.

(21) Appl. No.: 14/007,001

(22) PCT Filed: Mar. 21, 2012

(86) PCT No.: PCT/KR2012/002008
§ 371 (c)(1),
(2), (4) Date: Sep. 24, 2013

(87) PCT Pub. No.: WO2012/134093
PCT Pub. Date: Oct. 4, 2012

(65) Prior Publication Data
US 2014/0017147 A1    Jan. 16, 2014

(30) Foreign Application Priority Data

Mar. 25, 2011    (KR) .................... 10-2011-0026731

(51) Int. Cl.
*B01L 3/02*     (2006.01)
*G01N 33/50*    (2006.01)
*G01N 1/14*     (2006.01)
(Continued)

(52) U.S. Cl.
CPC ............ *G01N 33/50* (2013.01); *A61B 10/0038* (2013.01); *B01L 3/505* (2013.01); *B01L 3/50825* (2013.01); *C12M 33/02* (2013.01); *G01N 1/14* (2013.01); *G01N 1/38* (2013.01); *A61B 10/0096* (2013.01); *B01L 3/0272* (2013.01); *B01L 2200/026* (2013.01); *B01L 2300/042* (2013.01);
(Continued)

(58) Field of Classification Search
CPC ................ G01N 2035/1053; B01L 2300/0681
USPC .............................. 422/513, 521; 222/189.06
See application file for complete search history.

(56) References Cited

U.S. PATENT DOCUMENTS 5,120,438 A *   6/1992   Nakagawa et al. ........... 210/256
6,296,764 B1 *  10/2001  Guirguis et al. ........... 210/323.1
(Continued)

FOREIGN PATENT DOCUMENTS

| JP | 2000-254208 A | 9/2000 |
| JP | 2004-004014 A | 1/2004 |
| JP | 2009-154918 A | 7/2009 |
| JP | 2011-033114 A | 2/2011 |

OTHER PUBLICATIONS

International Search Report mailed Oct. 18, 2012, issued in corresponding International Patent Application No. PCT/KR2012/002008.

*Primary Examiner* — Jill Warden
*Assistant Examiner* — Brittany Fisher
(74) *Attorney, Agent, or Firm* — Stein IP, LLC

(57) ABSTRACT

The present invention discloses an integrated sampling and dispensing device comprising a flexible container, a dropper with a sampling rod and a sample removing vessel disposed therebetween. The device of the present invention can be conveniently used for collecting specimen and dispensing the same after a reaction in a single device by simple manipulation of severing the sampling rod and turning the container upside down. Also by using the present device a constant amount of specimen can be used for each reaction which leads to a reliable and reproducible result.

13 Claims, 6 Drawing Sheets

(51) Int. Cl.
*G01N 1/38* (2006.01)
*C12M 1/30* (2006.01)
*B01L 3/00* (2006.01)
*A61B 10/00* (2006.01)

(52) U.S. Cl.
CPC .... *B01L 2300/046* (2013.01); *B01L 2400/0683* (2013.01)

(56) References Cited

U.S. PATENT DOCUMENTS

| | | | |
|---|---|---|---|
| 7,040,511 B1 * | 5/2006 | Petit | 222/189.09 |
| 2003/0077838 A1 * | 4/2003 | Pressman et al. | 436/177 |
| 2005/0195684 A1 * | 9/2005 | Mayer | 366/197 |

* cited by examiner

INTEGRATED SAMPLING AND DISPENSING DEVICE

CROSS-REFERENCE TO RELATED APPLICATIONS

The present application is a national stage application of International Patent Application No. PCT/KR2012/002008, filed Mar. 21, 2012, and claims the benefit of Korean Patent Application No. 10-2011-0026731, filed Mar. 25, 2011, in the Korean Intellectual Property Office, the disclosure of which are incorporated herein.

BACKGROUND OF THE INVENTION

1. Field of the Invention

The present invention generally relates to an integrated sampling and dispensing device, and more particularly, to an integrated sampling and dispensing device by which collecting specimen and dispensing the same after a reaction is performed in a single device.

2. Description of the Related Art

Various chemical or biochemical tests are developed for measuring biological indicators/markers present in biological samples that are associated with a development of particular diseases, general health status, or infection. Such tests are generally performed through multiple stages of chemical reactions and/or often require physical manipulations, which involve various reagents and tools. For example, when biochemical substances, such as occult blood included in fecal matter or mucus, specific chemicals, or proteins, are detected, physical manipulation that required includes several stages of collecting biological sample, dispensing the sample to a container for a reaction with one or more of test reagents of interest, and transferring and applying the reaction product from the container to a test device for analysis.

Conventional devices used for collecting samples for a test do not provide means for taking accurate amount of sample or need a separate element to dispense the sample after a reaction for analysis. This has caused inconvenience to the user in terms of handling and quality control and also increased the manufacturing cost of the device which resulted in increasing the total cost of analysis.

One conventional device includes a container body having two ends, one ends at the bottom is closed and the other end at the top is open and having a space formed therein and a first cap that closes the open end of the container body, wherein the first cap has a collection member mounted thereon for sampling specimen and the collection member has an outlet formed at one end and several grooves formed on a surface thereof in a region closed to the other end of the collection member and a second cap for closing the outlet. According to the conventional device, the collection member mounted on the first cap is used for collecting specimen of interest at the end having the grooves and the first cap is replaced on the open end of the container body allowing the specimen collected and a reagent in the container body to react. Thereafter, for analysis, the second cap is removed and the container body is turned upside down to discharge the reaction product therein through the outlet. However, the device does not provide a means to accurately control the amount of the specimen to be used for the reaction, which resulted in a low reliable and reproducible result due to the inconsistent amount of the specimen used for reaction.

According to other conventional device, to solve the foregoing problems, a means to control the amount of specimen used for reaction is implemented. In this case, however, an outlet for discharge of the reaction product is usually formed on one end of a container and not on a collection member. For example, the bottom of a container body is closed by a cap which can be removed for dispensing the reaction product, which is inconvenient to use and increases the manufacturing cost of the device. A need therefore exists for a convenient and reliable device that requires minimal manipulation, integrating means for accurately control the amount of specimen used for a reaction and dispensing into one system.

SUMMARY OF THE INVENTION

The present integrated sampling and dispensing device can be conveniently used for collecting specimen and dispensing the same after a reaction in a single device by simple manipulation of severing the sampling rod and turning the container upside down. Also by using the present device a constant amount of specimen can be used for each reaction which leads to a reliable and reproducible result.

In one aspect, the present disclosure provides an integrated sampling and dispensing device comprising: flexible container having an open end for carrying out a reaction of interest with a specimen; dropper having a rod longitudinally mounted therethrough, the rod having a first end being disposed inwardly of the container and a second end being disposed outwardly of the container and a collection member formed on an exterior surface of the rod adjacent to the first end for collecting a specimen, an opening formed on the second end for dispensing the reaction product, a cavity extended from the opening defining the inner surface of the rod and a severing member formed on the exterior surface of the rod where the cavity is formed, wherein the severing member is capable of being severed by the application of force against the severing member; and a sample removing vessel disposed between the flexible container and the dropper, the sample removing vessel having a first side and a second side, the first side sealing the open end of the flexible container, the second side being removably connected to the dropper, and a hole therethrough for receiving the rod.

In one embodiment, the severing member includes at least one groove.

In other embodiment, the dropper further comprises a hollow therein.

In still other embodiment, the container and the sample removing vessel further include a raised element to mount the vessel and the dropper, respectively.

In still other embodiment, the container may be formed of a transparent or semi-transparent material.

In still other embodiment, the collection member includes at least one groove or a capillary formed within the rod near the first end.

According to one or more embodiments of the present invention, an integrated sampling and dispensing device includes An integrated sampling and dispensing device comprising: a transparent or semi-transparent flexible container having an open end for carrying out a reaction of interest with a specimen; a dropper having a rod longitudinally mounted therethrough, the rod having a first end being disposed inwardly of the vessel and a second end being disposed outwardly of the container and a collection member having at least one groove formed on an exterior surface of the rod adjacent to the first end or a capillary formed within the rod adjacent to the first end for collecting a specimen, an opening formed on the second end for dispensing the reaction product, a cavity extended from the opening defining the inner surface of the rod and a severing member having formed on the exterior surface of the rod where the cavity is formed, wherein the severing member is capable of being severed by the application of force against the severing member; and a sample removing vessel disposed between the flexible vessel and the dropper, the sample removing vessel having a first side and a second side, the first side sealing the open end of the flexible vessel, the second side being removably connected to the dropper, and a hole formed therethrough for receiving the rod, wherein the container and the sample removing vessel further include a raised element to engage the vessel on top of the container and engage the dropper on top of the vessel, respectively.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION OF THE EMBODIMENTS

Figure 1:
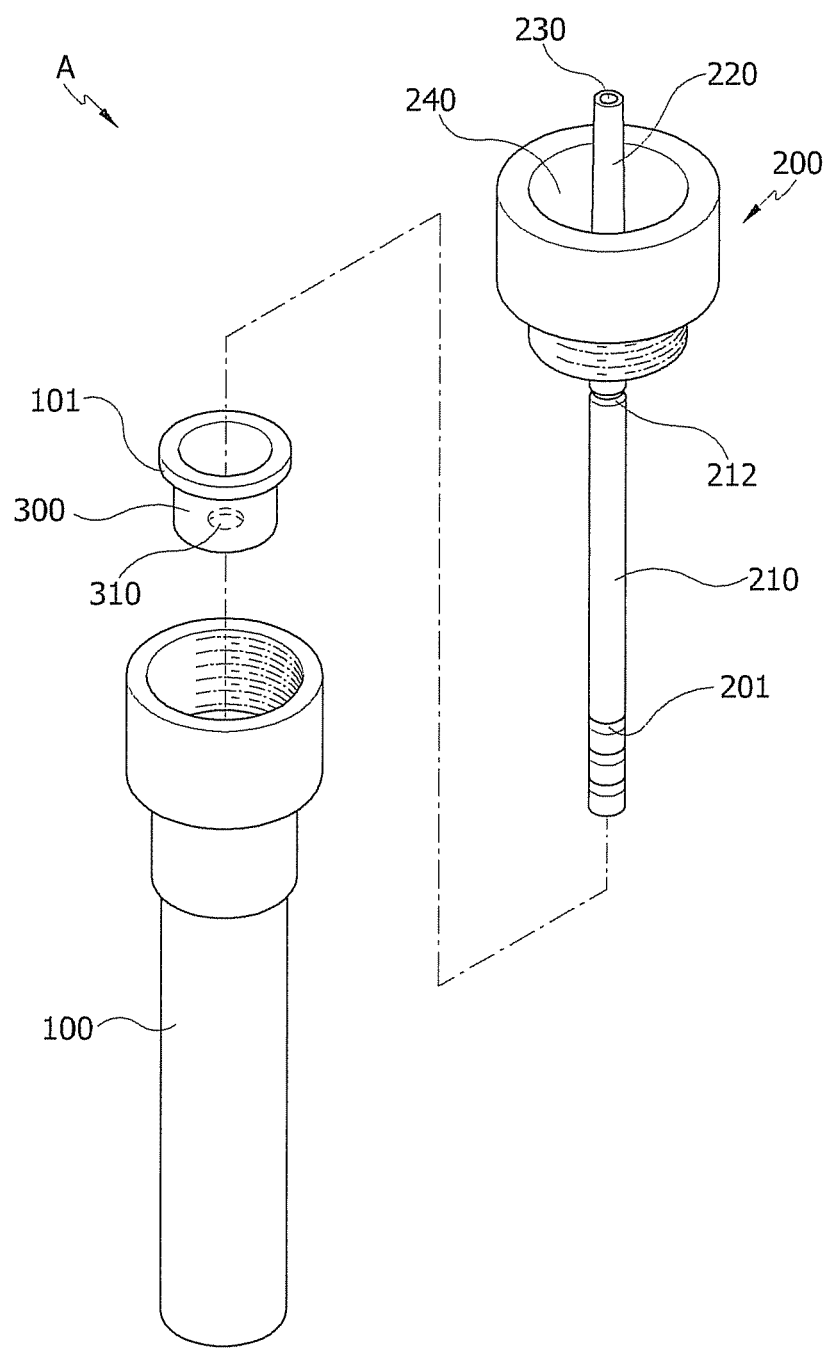
FIG. 1 is an exploded perspective view showing each element constituting an integrated sampling and dispensing device according to an exemplary embodiment of the present invention.

Reference will now be made in detail to the present embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are described below in order to explain the present invention by referring to the figures.

Figure 2:
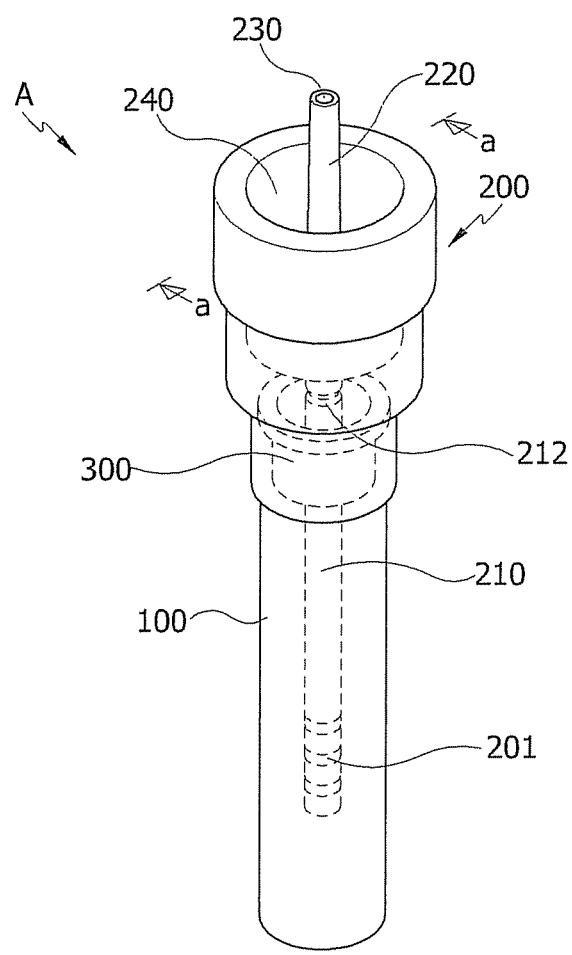
FIG. 2 is a perspective view of an integrated sampling and dispensing device according to an exemplary embodiment of the present invention wherein the elements as shown in FIG. 1 are assembled.
Figure 3:
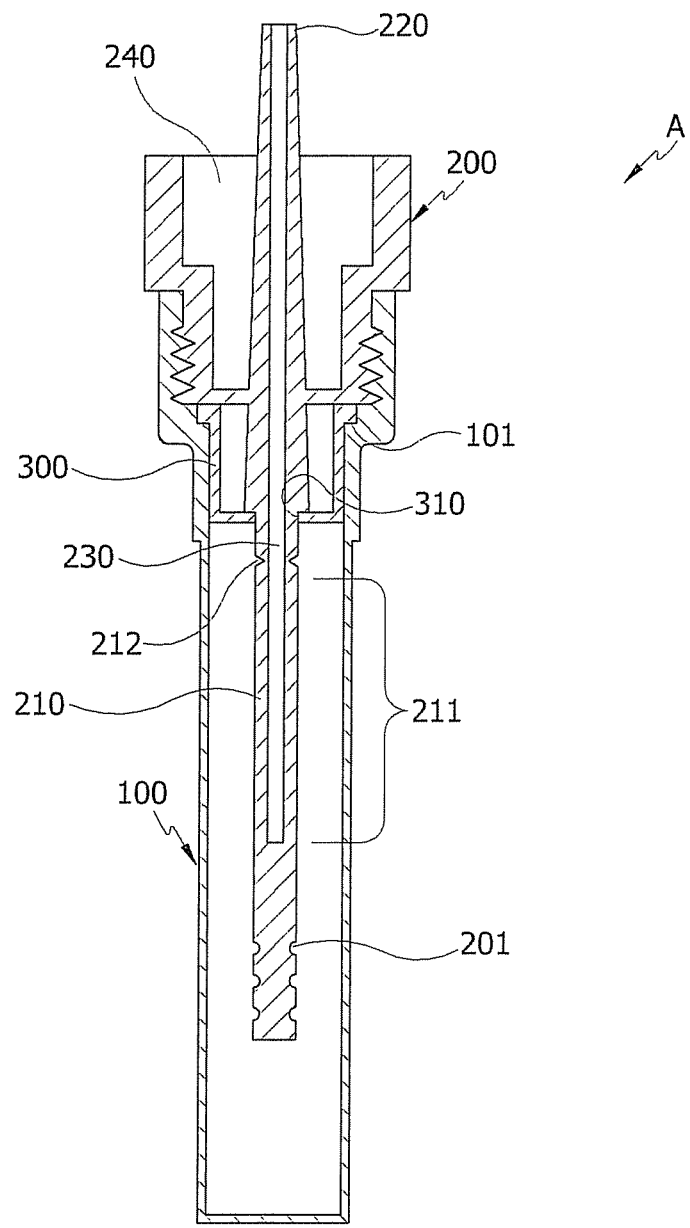
FIG. 3 is a cross-sectional view taken along a line a-a of FIG. 2.
Figure 4:
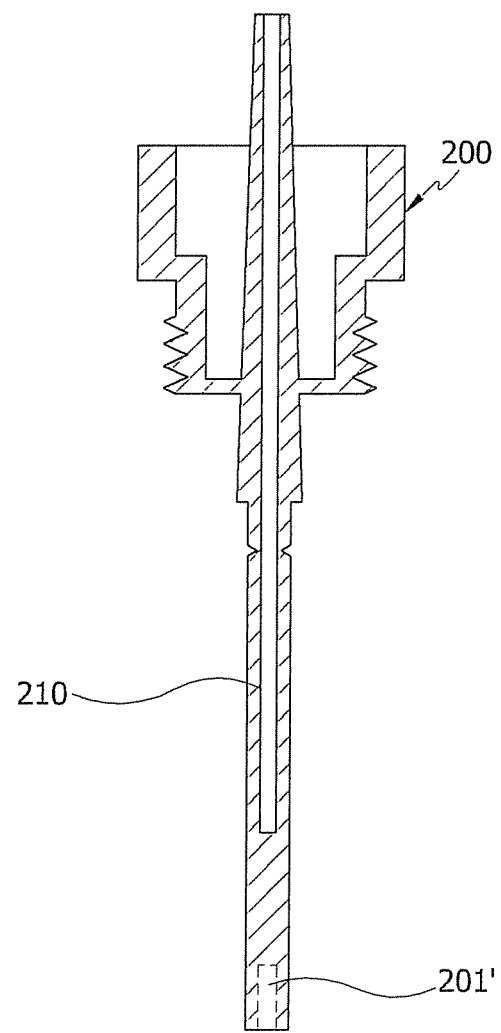
FIG. 4 is a cross-sectional view showing a dropper according to another exemplary embodiment of the present invention.
Figure 5:
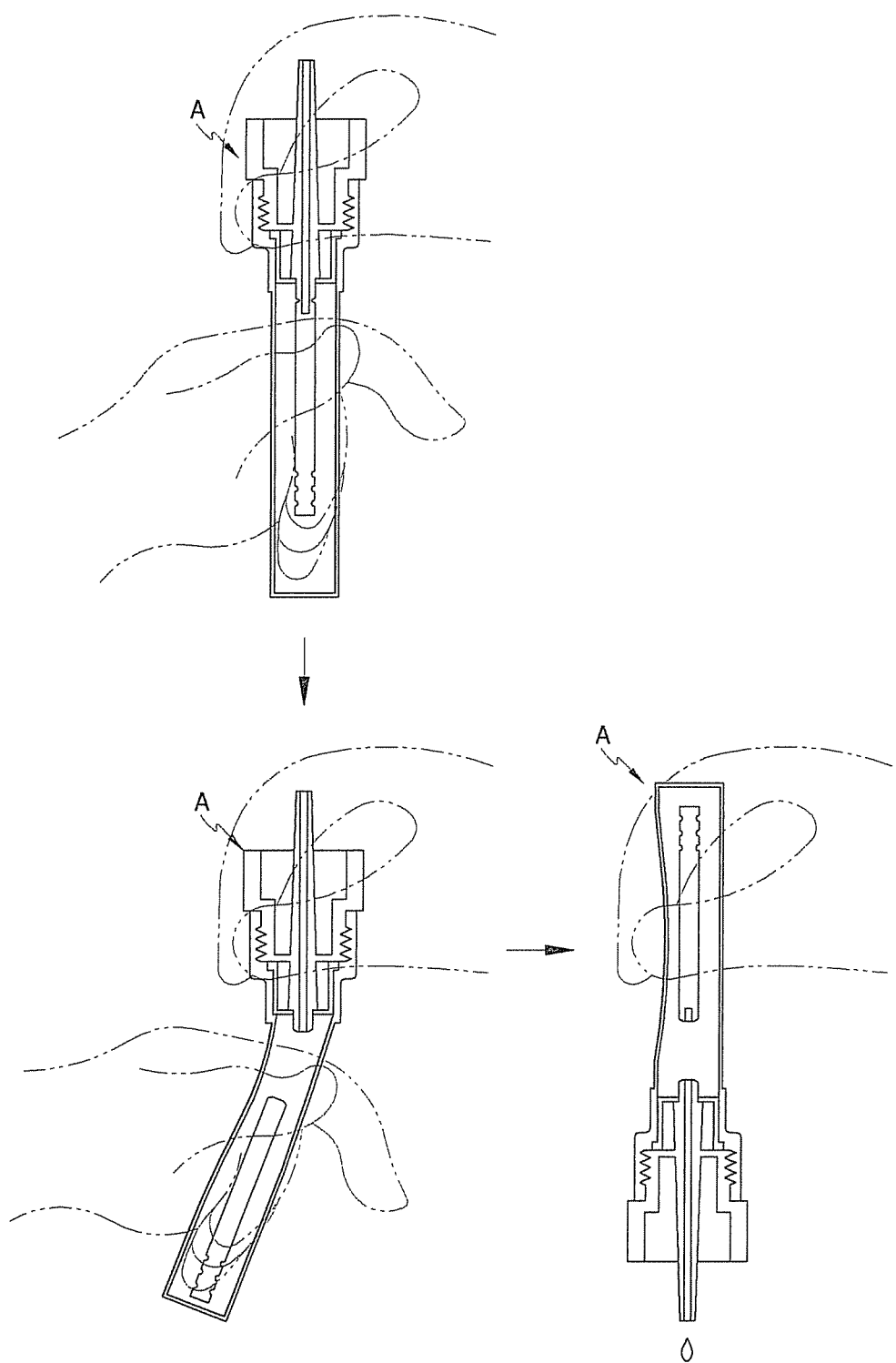
FIG. 5 is a schematic diagram showing one exemplary usage of the present sampling and dispensing device according to an exemplary embodiment of the present invention.
Figure 6:
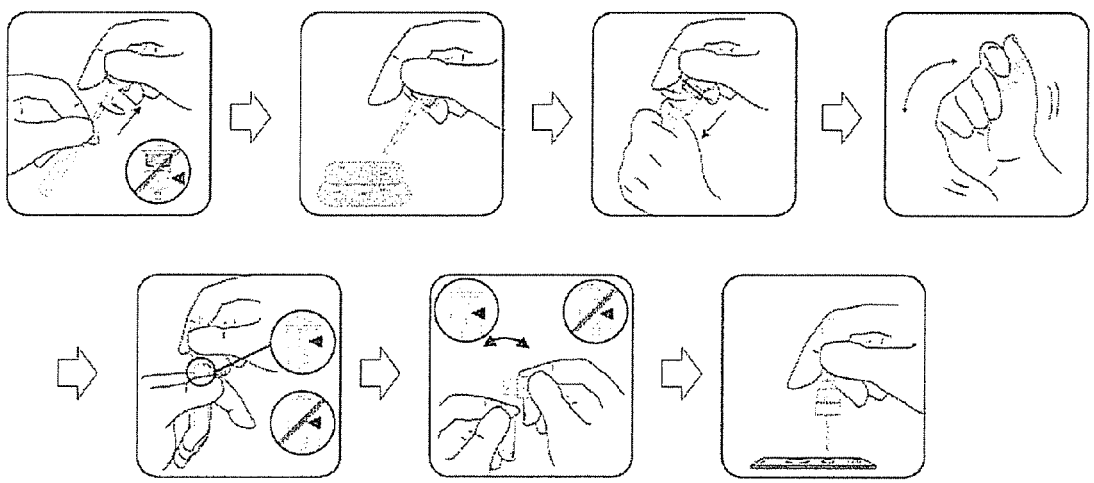
FIG. 6 is a schematic diagram showing one exemplary usage of the present sampling and dispensing device according to an exemplary embodiment of the present invention.

FIG. 1 is an exploded perspective view of an integrated sampling and dispensing device according to an exemplary embodiment of the present invention, FIG. 2 is a perspective view showing an assembled state of the elements as depicted in FIG. 1, FIG. 3 is a cross-sectional view taken along a line a-a of FIG. 2, FIG. 4 is a cross-sectional view showing a dropper according to another exemplary embodiment of the present invention. FIG. 5 is a schematic diagram showing a use state of an integrated sampling and dispensing device according to one exemplary embodiment of the present invention, and FIG. 6 is a diagram showing, in a stepwise manner, an exemplary usage of an integrated sampling and dispensing device according to one exemplary embodiment of the present invention.

As shown in FIGS. 1 through 5, the present integrated sampling and dispensing device A includes a flexible container 100 having an open end and a dropper 200 having a sampling rod longitudinally or mounted therethrough, preferably perpendicular to the surface of the dropper 200.

The container 100 has a closed bottom and an open end forming a space therein and is used for receiving a specimen and a reagent and for carrying out a reaction therebetween. The specimen may be in a solid, semi-solid or liquid form.

The container 100 may be formed of, but not limited to, a transparent or semi-transparent material such that the interior of the container 100 can be seen from the outside.

In one embodiment, female threads and male threads may be formed on the container body 100 and the dropper 200, respectively, such that the container body 100 and the dropper 200 are screw-coupled to seal the receiving space of the container body 100.

That is, the open end of the container 100 may be sealed by the dropper 200 to prevent a specimen within the container 100 from leaking from the container 100.

In one embodiment, the dropper 200 includes a rod having a first and a second end, and having a collection member 210 formed on a surface of the rod adjacent to the first end, an opening 220 formed on the second end for dispensing the reaction product.

Further a cavity 230 is formed extending from the opening 220 defining the inner surface of the rod and may have a cross-sectional shape of rectangular "⊏" or "U".

The rod is longitudinally mounted through the dropper 200 and the collection member 210 formed near the first end of the rod is disposed inwardly into the interior of the container 100 and the opening 220 formed on the second end is disposed outwardly of the container. The cavity 230 that is extending longitudinally along the length of the rod from the opening may have various lengths. A severing member 211 is formed on the exterior surface of the rod where the cavity is formed such that when the rod is severed at the severing member by the application of force or pressure or shearing stress against the severing member, the interior of the container 100 then is communicated with the cavity 230 and the reaction product inside the container 100 can be discharged through the opening 220. The severing member 211 may be formed at a desired position along the length of the rod as long as the contents of the container can be discharged through the opening 220 when the container 100 has been turned upside down. The rod may be made of a high-rigidity material so as to be easily broken by the application of shearing stress.

In one embodiment, the severing member 211 may include at least one groove 212, or at least one recessed line or at least one recessed curve to which the shearing forced is applied. The severing groove 212 may be formed at a desired position along the length of the rod as long as the contents of the container can be discharged through the opening 220 when the container 100 has been turned upside down. The groove 212 is for severing the rod at the severing member 211 and is formed on the exterior surface of the rod at a desired position as described above along the length of the rod. In one embodiment, the groove 212 is formed on the surface toward the second and of the rod and near a sample removing vessel 300 as described hereinafter. The severing groove 212 may have a variety of cross-sectional shape as long as a shearing stress can be applied against it to sever the rod and in one embodiment has a cross-sectional shape of "V" as shown in FIG. 3 without being limited thereto.

Referring to FIG. 5, according to one embodiment of the present integrated sampling and dispensing device A, a user holds the flexible container 100 and presses the container between the fingers and at the same time bends the rod by the severing member 211 or groove 212 so that the shearing stress applied to the severing groove can sever the rod at the severing member, exposing the cavity 230 which is now in communication with the interior of the container 100. Thus the contents of the container can be discharged or dispensed through the opening 220.

Hence, by a simple manipulation of the rod at the severing member 211, the cavity 230 of the rod can be exposed to make it communicated with the interior of the container 100 and the content of the container can be discharged through the opening 220, which increases the convenience of the user for handling and preparing the sample or specimen for analysis.

In one embodiment, the dropper 200 may further include a hollow or a space 240 formed therein and the opening 220 formed on the second end of the rod is disposed outwardly from the dropper.

The hollow or space 240 in the dropper 200 is to provide a convenient discharging of the reaction product after the completion of a reaction in the container 100. Also the hollow or space 240 may be used to install the present device A to an analytical instrument of interest (not shown) for further analysis.

Further the present device further includes a sample removing vessel 300 disposed between the container 100 and the dropper 200. The sample removing vessel 300 have a hole 310 therethrough for receiving the rod having a collection member 210. The size of hole 310 is equal or smaller than an outer circumferential size of the sampling rod. The removing vessel 300 may be molded by an appropriate injection process as one unit comprising the vessel 300 and the container 100. The female threads and male threads may be formed on the sample removing vessel 300 and the dropper 200, respectively, such that the sample removing vessel 300 and the dropper 200 are screw-coupled to seal the interior of the container 100.

The removing vessel 300 is used to remove the excess specimen or sample collected on the collection member 210. By passing the collection member 210 through the hole 310 in the vessel 300, the excess specimen on the surface of the collection member 210 is removed leaving the sample present only in the grooves or recesses formed on the collection member 210. Thus exactly the same amount of sample is able to be used for each reaction performed in the container, leading to the reliable and reproducible analysis.

When the collection member of the sampling rod 210 is inserted through the hole 310, the outer circumferential surface of the sampling rod is in contact with the inner circumferential surface of the hole 310, such that the extra specimen present on the surface of the collection member 210 can be removed. The hole 310 may be formed of a flexible material such as polyethylene to increase the tightness of the contact, in which case, the diameter of the hole 300 may be formed to be smaller than that of the rod due to the flexibility provided by the material.

In one embodiment, the container 100 and the sample removing vessel 300 may further includes a raised element 101 to assemble each part of the present device A for example to mount the vessel on top of the container and to mount the dropper on top of the vessel, respectively. The raised element allows the vessel and the dropper to be inserted to a predetermined depth when mounting the same to each corresponding part as described. Further the collection member 210 includes at least one groove 201. In one embodiment plurality of grooves 201 are formed having the equal interval between the grooves along a longitudinal direction of the rod at the region near the first end of the rod.

Further, referring to FIG. 4, the collection member may further include a capillary 201' formed within the rod near the first end so as to be able to collect specimen. The dimension of capillary may vary depending on the types of sample or the amount of sample to be collected. The capillary 201' is a well-known structure and thus will not be described in detail.

In the present invention, components other than the container 100 may be formed of a rigid material such as polypropylene, but a flexible material such as polyethylene is not excluded to provide and improve the property such as contact, or airtightness. Also any of opaque, transparent, and semi-transparent materials may be used. The container 100 is fabricated with a flexible material such as polyethylene, which may be pressed without being broken to apply a shearing stress to the severing member 211 or the groove 212 of the sampling rod, and the container 100 is particularly fabricated with a transparent or semi-transparent material such that the inside of the container 100 may be seen from the outside.

Hereinafter, exemplary sampling and dispensing procedures using the integrated sampling and dispensing device A according to one embodiment of the present invention will be described in brief with reference to FIGS. 5 and 6.

First, the collection member 210 of the rod coupled to the dropper 200 is dipped into a liquid or solid specimen of interest to collect the specimen on the groove 201 formed on the surface the rod. The specimen includes, but is not limited to, a viscous biological material such as feces, expectoration, saliva, and nasal discharge, and a liquid biological material such as whole blood, plasma, and serum. When the liquid specimen is used, the reagent used for a reaction with the specimen may be present in a dry state in the container 100 and upon addition of the collected specimen; the specimen is mixed and reacts with the dry reagent. Alternatively, the liquid specimen may be collected using the sampling rod having the capillary 201' through which the specimen is moved to the capillary 201' by a capillary action.

Next, the dropper 200 with the specimen collected on the collection member 210 of the rod is inserted into the container 100 through the hole 310 formed on the sample removing vessel 300. The excessive specimen collected on the rod is then removed while the rod is passing through the hole 310. Then, the container 100 may be shaken to start or facilitate the reaction between the reagent and the specimen.

Next, as shown in FIG. 5, pressure is applied to the container using hands and by bending the severing member 211; the rod 210 is severed at the severing member 211. When the groove 212 is formed on the severing member 211, the user bends the rod at the groove 212 so that the shearing stress applied to the severing groove can sever the rod at the severing member, exposing the cavity 230 which is now in communication with the interior of the container 100. Alternatively, as shown in FIG. 6, the dropper 200 is detached from the container 100 while the part of the rod is still in the container and by moving the dropper slightly left and right, the sampling rod is severed at the severing member 211, or at the groove 212, exposing the cavity 230 which is now in communication with the interior of the container 100.

Lastly, the product of reaction in the container 100 is now discharged or dispensed for analysis through the opening 220 by turning the device A upside down and lightly squeezing the container.

While a few embodiment of the present invention have been shown and described, it would be appreciated by those skilled in the art that changes may be made in this embodiment without departing the principles and spirit of the invention, the scope of which is defined in the claims and their equivalents.

For example, in the foregoing description, the integrated sampling and dispensing device according to one embodiment of the present invention is used in medical diagnosis/detection fields, but it may also be applied to various other industrial fields where the present device is applicable.

With respect to the use of substantially any plural and/or singular terms herein, those having skill in the art can translate from the plural to the singular and/or form the singular to the plural as is appropriate to the context and/or application. The various singular/plural permutations may be expressly set forth herein for sake of clarity.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An integrated sampling and dispensing device comprising:
   a flexible container having an open end for carrying out a reaction of interest with a specimen;
   a dropper having a rod longitudinally mounted therethrough, the rod having a first end being disposed inwardly of the container and a second end being disposed outwardly of the container and a collection member formed on an exterior side surface of the rod adjacent to the first end for collecting a specimen, an opening formed on the second end for dispensing the reaction product, a cavity extended from the opening defining the inner surface of the rod and a severing member formed on the exterior side surface of the rod where the cavity is formed, wherein the severing member is configured to be severed by pressure applied thereon thereby exposing the cavity; and
   a sample removing vessel disposed between the flexible container and the dropper, the sample removing vessel having a first side and a second side, the first side sealing the open end of the flexible container, the second side being removably connected to the dropper, and a hole therethrough for receiving the rod.

2. The integrated sampling and dispensing device of claim 1, wherein the severing member includes at least one groove.

3. The integrated sampling and dispensing device of claim 1, wherein the dropper further comprises a hollow therein.

4. The integrated sampling and dispensing device of claim 1, wherein the container and the sample removing vessel further include a raised element to mount the vessel and the dropper, respectively.

5. The integrated sampling and dispensing device of claim 1, wherein the container is made of a transparent or semi-transparent material.

6. The integrated sampling and dispensing device of claim 1, wherein the collection member includes at least one groove or a capillary formed within the rod near the first end.

7. An integrated sampling and dispensing device comprising:
   a transparent or semi-transparent flexible container having an open end for carrying out a reaction of interest with a specimen;
   a dropper having a rod longitudinally mounted therethrough, the rod having a first end being disposed inwardly of the vessel and a second end being disposed outwardly of the container and a collection member having at least one groove formed on an exterior side surface of the rod adjacent to the first end or a capillary formed within the rod adjacent to the first end for collecting a specimen, an opening formed on the second end for dispensing the reaction product, a cavity extended from the opening defining the inner surface of the rod and a severing member having formed on the exterior side surface of the rod where the cavity is formed, wherein the severing member is configured to be severed by pressure applied thereon thereby exposing the cavity; and
   a sample removing vessel disposed between the flexible vessel and the dropper, the sample removing vessel having a first side and a second side, the first side sealing the open end of the flexible vessel, the second side being removably connected to the dropper, and a hole formed therethrough for receiving the rod,
   wherein the container and the sample removing vessel further include a raised element to engage the vessel on top of the container and engage the dropper on top of the vessel, respectively.

8. A sampling and dispensing device comprising:
   a flexible container formed with an opening;
   a dropper for closing the opening of the flexible container, the dropper including a sampling rod that is disposed in the flexible container, the sampling rod being formed therein with a cavity passage that is extended from a hole at a longitudinal end of the sampling rod along a longitudinal direction thereof; and
   an intermediate member disposed between the flexible container and the dropper, the intermediate member being formed with a through-hole into which the sampling rod is inserted,
   wherein the sampling rod is provided thereon with a surface structure that is configured for breaking the sampling rod into two parts by pressing thereon, the surface structure being located on an outside surface of the sampling rod beneath which the cavity passage exists.

9. The sampling and dispensing device of claim 8, wherein the surface structure includes at least one groove.

10. The sampling and dispensing device of claim 8, wherein the dropper includes a hollow that defines an inner surface thereof, the longitudinal end of the sampling rod being passed through the hollow of the dropper and protruded over an end of the dropper.

11. The sampling and dispensing device of claim 8, wherein the flexible container and the intermediate member respectively have a stopper structure.

12. The sampling and dispensing device of claim 8, wherein the flexible container is made of transparent or translucent material.

13. The sampling and dispensing device of claim 8, wherein the sampling rod is provided with at least one sampling groove thereon or a capillary therein.

* * * * *